US009491997B2

United States Patent
Yiu

(10) Patent No.: US 9,491,997 B2
(45) Date of Patent: *Nov. 15, 2016

(54) DRUM ASSEMBLY, COSMETIC DEVICE WITH DRUM ASSEMBLY, AND BATTERY COMPARTMENT FOR COSMETIC DEVICE

(71) Applicant: Soft Lines International, Ltd., Kowloon (HK)

(72) Inventor: Wai Wah Yiu, Kowloon (HK)

(73) Assignee: SOFT LINES INTERNATIONAL, LTD., Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 14/478,958

(22) Filed: Sep. 5, 2014

(65) Prior Publication Data

US 2015/0150352 A1 Jun. 4, 2015

Related U.S. Application Data

(60) Provisional application No. 61/910,826, filed on Dec. 2, 2013, provisional application No. 62/001,337, filed on May 21, 2014.

(51) Int. Cl.
*A45D 29/05* (2006.01)
*A45D 29/14* (2006.01)
(Continued)

(52) U.S. Cl.
CPC .............. *A45D 29/05* (2013.01); *A45D 29/14* (2013.01); *A61B 17/54* (2013.01); *A61B 2017/00398* (2013.01); *A61B 2017/00734* (2013.01); *A61B 2017/320004* (2013.01)

(58) Field of Classification Search
CPC ............... A61B 2017/320004; A61B 17/54; A45D 29/00; A45D 29/007; A45D 29/04; A45D 29/05; A45D 29/06; A45D 29/11; A45D 29/14; A45D 29/17; A45D 2029/045; A45D 34/041; A45D 40/26; A45D 40/205; A45D 2200/1054; A45D 2200/1063; B24D 9/00
USPC ....... 132/73.6, 200, 73, 73.5, 75, 75.3, 75.6, 132/75.8, 76.4, 317, 318, 320; 606/9, 131, 606/133; 119/608, 609, 620, 663; 451/119, 451/120, 162, 177, 358, 344, 541
See application file for complete search history.

(56) References Cited

U.S. PATENT DOCUMENTS 1,822,631 A * 9/1931 Roig .................................. 15/23
1,829,338 A * 10/1931 Bynum ......................... 132/76.5
(Continued)

FOREIGN PATENT DOCUMENTS

| CN | 200953919 | 10/2007 |
| CN | 203399787 | 1/2014 |

(Continued)

OTHER PUBLICATIONS

International Search Report and Written Opinion for PCT Application No. PCT/IB2014/002837, mailed Apr. 28, 2015, 11 pages.
(Continued)

*Primary Examiner* — Robyn Doan
(74) *Attorney, Agent, or Firm* — Foley & Lardner LLP

(57) ABSTRACT

A cosmetic device is provided. The cosmetic device includes a housing; a drum assembly rotatably coupled to the housing, the drum assembly including an abrasive outer surface and a deformable portion disposed below the abrasive outer surface; and a drive system configured to rotate the drum assembly relative to the housing.

8 Claims, 12 Drawing Sheets

(51) Int. Cl.
  *A61B 17/54* (2006.01)
  *A61B 17/00* (2006.01)
  *A61B 17/32* (2006.01)

(56) References Cited

U.S. PATENT DOCUMENTS

| | | | | |
|---|---|---|---|---|
| 1,915,305 | A * | 6/1933 | Gallagher | 132/75.8 |
| 2,008,894 | A * | 7/1935 | Bergstrom | 464/52 |
| 2,056,379 | A * | 10/1936 | Acocella | 132/73.6 |
| 2,596,335 | A * | 5/1952 | Kessler | 464/53 |
| 2,597,526 | A * | 5/1952 | Kessler | 132/75.8 |
| 3,129,541 | A | 4/1964 | Field | |
| 3,311,117 | A | 3/1967 | Thompson | |
| 3,420,250 | A | 1/1969 | Holmes | |
| 3,916,920 | A | 11/1975 | Tsukamoto | |
| 4,034,769 | A | 7/1977 | Nishimura | |
| 4,137,926 | A * | 2/1979 | Pao | 132/73.6 |
| 4,344,202 | A * | 8/1982 | Hayat | A61C 17/26 15/22.1 |
| 4,381,792 | A * | 5/1983 | Busch et al. | 132/75.6 |
| 4,440,182 | A | 4/1984 | Holm | |
| 4,683,897 | A * | 8/1987 | McBride | A61B 17/54 132/73 |
| 4,854,334 | A | 8/1989 | Su | |
| 4,874,001 | A * | 10/1989 | Ferraris | 132/75.8 |
| 5,161,552 | A * | 11/1992 | Kathuria | 132/73.6 |
| 5,163,455 | A * | 11/1992 | Pointe et al. | 132/76.4 |
| 5,287,863 | A * | 2/1994 | La Joie et al. | 132/76.4 |
| 5,439,013 | A * | 8/1995 | Hoover | 132/76.5 |
| 5,588,453 | A * | 12/1996 | Fraysher | 132/76.4 |
| 5,652,184 | A | 7/1997 | Goto et al. | |
| 5,899,210 | A * | 5/1999 | Letherby et al. | 132/76.4 |
| 6,047,702 | A * | 4/2000 | Pennington | 132/76.4 |
| 6,050,270 | A | 4/2000 | Tyshenko, Jr. | |
| 6,062,229 | A * | 5/2000 | Kandratavich et al. | 132/73.6 |
| 6,162,117 | A * | 12/2000 | Vo | 451/358 |
| 6,471,712 | B2 * | 10/2002 | Burres | 606/131 |
| 6,523,546 | B2 * | 2/2003 | Jo et al. | 132/75.8 |
| 6,629,983 | B1 * | 10/2003 | Ignon | 606/131 |
| 6,640,811 | B2 | 11/2003 | Cho | |
| 6,679,271 | B2 * | 1/2004 | Choe | 132/76.4 |
| 7,033,169 | B2 | 4/2006 | Furney | |
| 7,267,125 | B2 | 9/2007 | Nevakshonoff | |
| 7,475,687 | B2 * | 1/2009 | Merten | 132/75.8 |
| 7,493,670 | B1 * | 2/2009 | Brogan | B24B 23/02 15/230 |
| 7,581,545 | B1 | 9/2009 | Moldawski et al. | |
| 7,789,092 | B2 * | 9/2010 | Akridge et al. | 132/200 |
| 8,201,565 | B2 * | 6/2012 | Fernandez et al. | 132/73.6 |
| 8,230,543 | B2 * | 7/2012 | Shrier et al. | 15/145 |
| 8,905,668 | B2 | 12/2014 | Edmondson et al. | |
| 2003/0102002 | A1 | 6/2003 | Cho | |
| 2004/0181241 | A1 * | 9/2004 | Jo et al. | 606/131 |
| 2006/0137703 | A1 * | 6/2006 | Kling | A45D 29/05 132/73.6 |
| 2007/0028936 | A1 * | 2/2007 | Kriser | A45D 29/05 132/76.4 |
| 2008/0173321 | A1 | 7/2008 | Le | |
| 2009/0126750 | A1 | 5/2009 | Pellereau | |
| 2010/0083975 | A1 | 4/2010 | Nguyen et al. | |
| 2010/0132728 | A1 * | 6/2010 | Busch | 132/75.8 |
| 2011/0021114 | A1 * | 1/2011 | McArdle et al. | 451/8 |
| 2011/0226268 | A1 | 9/2011 | Filonczuk | |
| 2011/0275282 | A1 | 11/2011 | Popov et al. | |
| 2012/0022556 | A1 * | 1/2012 | Sanchez-Martinez | 606/133 |
| 2013/0056016 | A1 * | 3/2013 | Guay et al. | 132/200 |
| 2013/0092182 | A1 * | 4/2013 | Stockbauer | 132/75.8 |
| 2014/0345637 | A1 * | 11/2014 | Laaly | A45D 34/04 132/73 |
| 2015/0072596 | A1 * | 3/2015 | Olberg et al. | 451/28 |
| 2015/0173484 | A1 * | 6/2015 | Fitzsimons et al. | 132/200 |

FOREIGN PATENT DOCUMENTS

| | | |
|---|---|---|
| CN | 203505864 | 4/2014 |
| CN | 204169260 | 2/2015 |
| EP | 1 982 613 | 10/2008 |
| GB | 2 457 679 | 8/2009 |
| WO | WO-2007/050342 | 5/2007 |

OTHER PUBLICATIONS

Extended European Search Report for EP Application No. 14821481.0 dated Jul. 25, 2016, 8 pages.

* cited by examiner

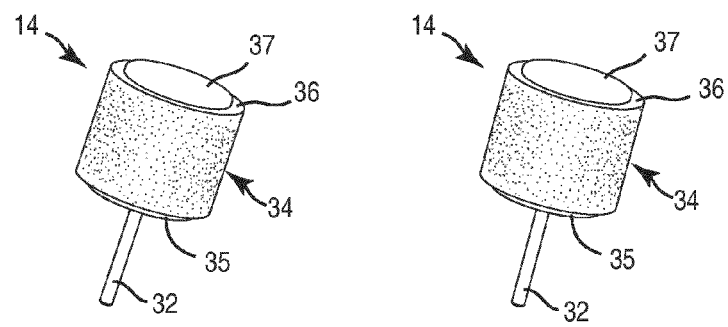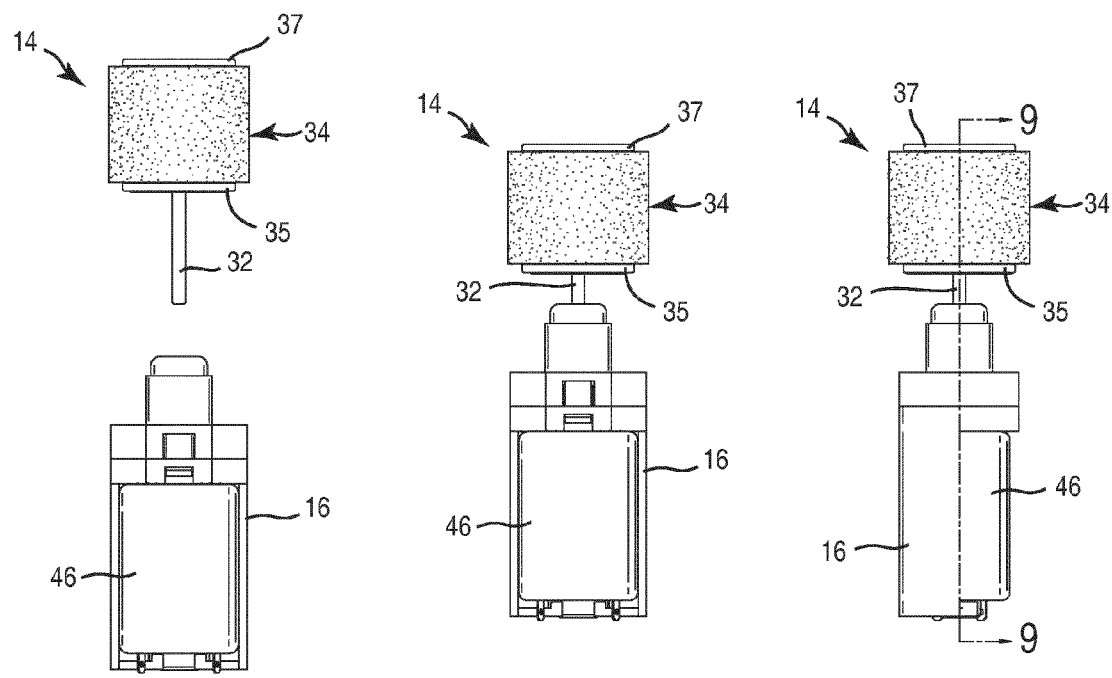

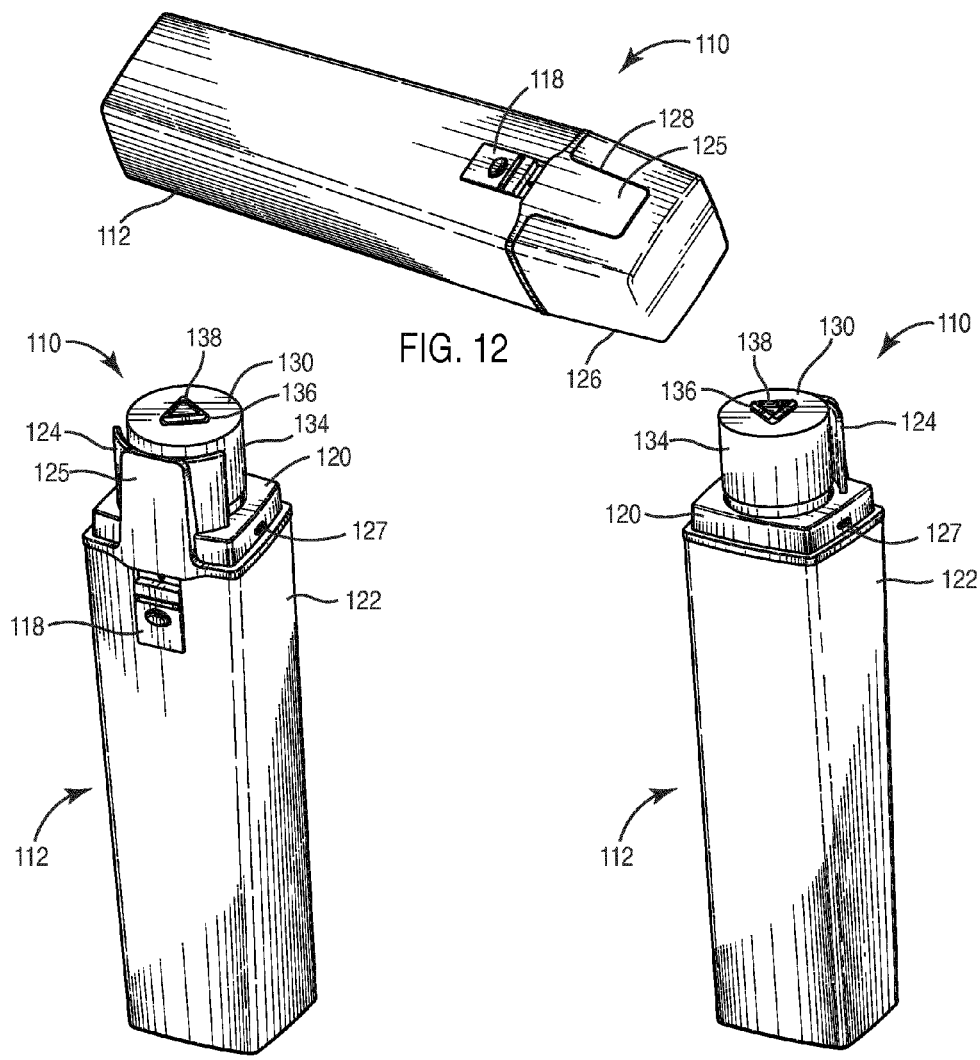
FIG. 12
FIG. 13 FIG. 14
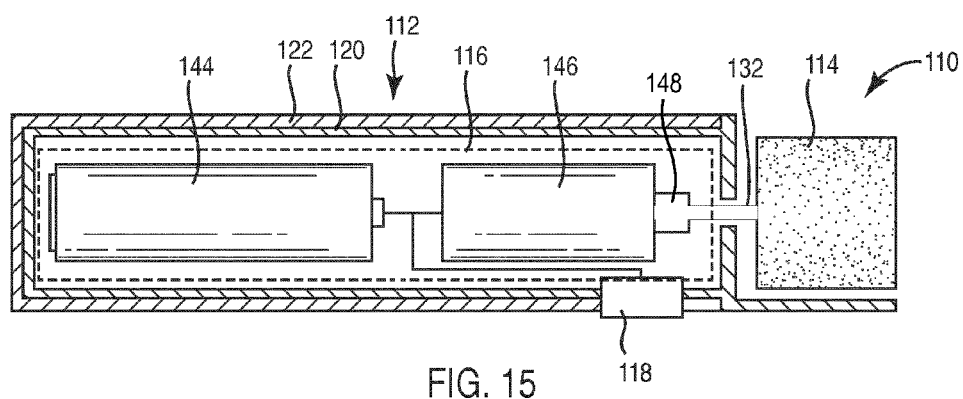
FIG. 15

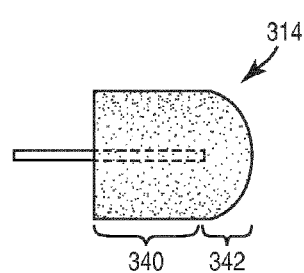
FIG. 21A
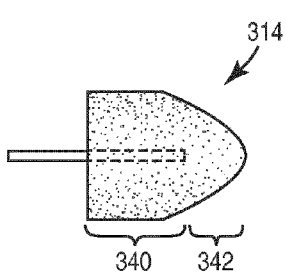
FIG. 21B
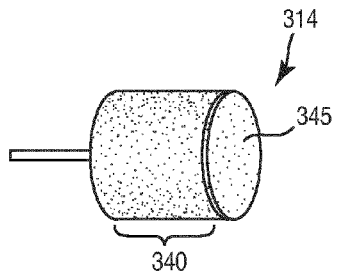
FIG. 21C
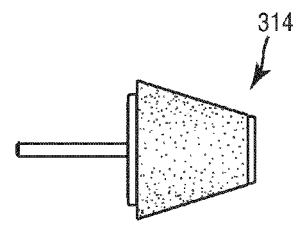
FIG. 21D
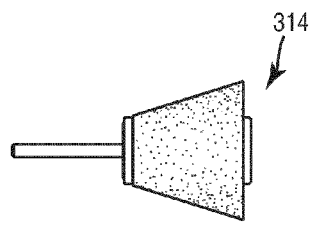
FIG. 21E
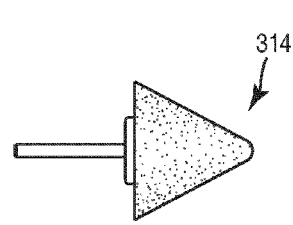
FIG. 21F
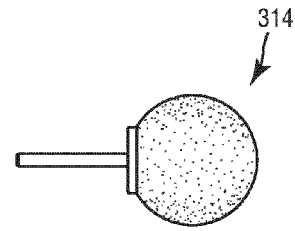
FIG. 21G
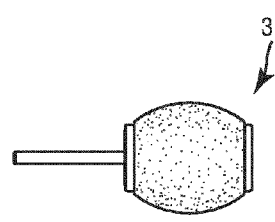
FIG. 21H
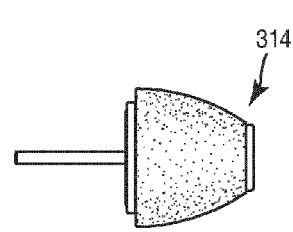
FIG. 21I
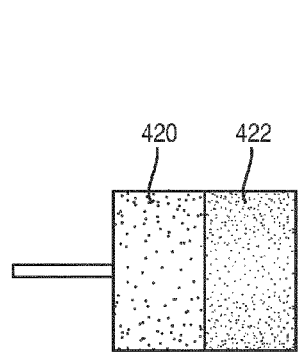
FIG. 22
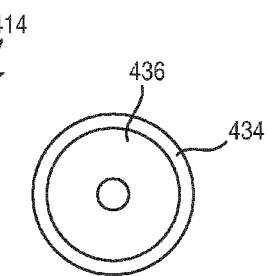
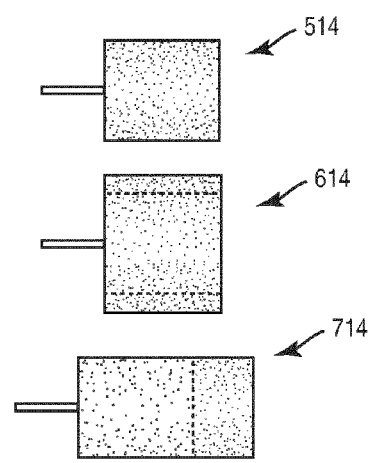
FIG. 23

DRUM ASSEMBLY, COSMETIC DEVICE WITH DRUM ASSEMBLY, AND BATTERY COMPARTMENT FOR COSMETIC DEVICE

CROSS-REFERENCE TO RELATED APPLICATIONS

This application claims the benefit and priority of U.S. Provisional Patent Application No. 61/910,826, filed Dec. 2, 2013, and U.S. Provisional Patent Application No. 62/001,337, filed May 21, 2014, both of which are incorporated by reference herein in their entireties.

BACKGROUND

One aspect of the present disclosure relates to abrasive drum assemblies, and cosmetic devices that use abrasive drum assemblies. More specifically, the aspect of the present disclosure relates to compressible or flexible drum assemblies that incorporate an abrasive outer surface and an underlying pliable, deformable, or flexible material.

Another aspect of the present disclosure relates generally to a battery compartment and more specifically to a battery compartment for a cosmetic device. Small electric devices powered by batteries may include an accessible battery compartment, allowing a user to replace disposable batteries or remove rechargeable batteries to recharge the batteries. The battery compartments of such devices may be accessed by removing a door or panel from the housing. The door or panel typically includes features such as ridges or surface texture that facilitates the sliding of the door relative to the housing or a recessed latch. Such features can protrude beyond the outer surface of the device or create voids in the outer surface of the device, which can make the device more uncomfortable to hold. Additionally, the seam line between the door or panel and the remainder of the housing can lessen the smooth contours of the device and its aesthetic appeal.

SUMMARY

One embodiment relates to a cosmetic device. The cosmetic device includes a housing; a drum assembly rotatably coupled to the housing, the drum assembly including an abrasive outer surface and a deformable portion disposed below the abrasive outer surface; and a drive system configured to rotate the drum assembly relative to the housing. The abrasive outer surface may include one of a sheet of abrasive material and a coating of abrasive material. The abrasive outer surface may include diamond abrasive particles. The abrasive outer surface may include abrasive particles provided at approximately 500 particles per square inch. The abrasive outer surface may include abrasive particles provided at approximately 1000 particles per square inch. The drum assembly may include a generally cylindrical drum, the drum including the abrasive outer surface and the deformable portion. The drum may include a recess and the drive system includes a drive shaft, wherein the drive shaft is received within the recess. The recess and the drive shaft may have corresponding shapes to prevent relative rotation between the drive shaft and the drum. The drum assembly may include a drive shaft and the drive system may include a drive member defining a recess, wherein the drive shaft may be received within the recess. The recess and the drive shaft may have corresponding shapes to prevent relative rotation between the drive shaft and the drum. The abrasive outer surface may include a first portion having a first abrasiveness and a second portion having a second abrasiveness different from the first abrasiveness. The first portion may include a first visual indication of the first abrasiveness and the second portion may include a second visual indication of the second abrasiveness. The deformable portion may be configured such that the abrasive outer surface and the deformable portion deform upon application of pressure during use of the device on a nail of a user. The deformable portion may include a first portion having a first compressibility and a second portion having a second compressibility different from the first portion. The drum assembly may be a first exchangeable drum assembly configured for removable and/or replaceable attachment to the housing, and may further include at least one second exchangeable drum assembly configured for removable and/or replaceable attachment to the housing. The second exchangeable drum assembly may differ from the first exchangeable drum assembly in abrasiveness. The second exchangeable drum assembly may differ from the first exchangeable drum assembly in compressibility. The second exchangeable drum assembly may differ from the first exchangeable drum assembly in a diameter. The second exchangeable drum assembly may differ from the first exchangeable drum assembly in a thickness of the deformable portions. The second exchangeable drum assembly may include a plurality of exchangeable drum assemblies.

Another embodiment relates to a drum assembly configured for rotatable use with a cosmetic device. The drum assembly includes an abrasive outer surface and a deformable portion disposed below the abrasive outer surface. The abrasive outer surface is rotatable by the cosmetic device to smooth and/or polish an outer layer of a nail of a user. The abrasive outer surface may include one of a sheet of abrasive material and a coating of abrasive material. The abrasive outer surface may include diamond abrasive particles. The abrasive outer surface may include abrasive particles provided at approximately 500 particles per square inch. The abrasive outer surface may include abrasive particles provided at approximately 1000 particles per square inch. The drum assembly may include a generally cylindrical drum, the drum including the abrasive outer surface and the deformable portion. The drum may include a recess configured to receive a drive shaft. The recess and the drive shaft may have corresponding shapes to prevent relative rotation between the drive shaft and the drum. The drum assembly may include a drive shaft configured to be received within a recess of a drive member. The recess and the drive shaft may have corresponding shapes to prevent relative rotation between the drive shaft and the drum. The abrasive outer surface may include a first portion having a first abrasiveness and a second portion having a second abrasiveness different from the first abrasiveness. The first portion may include a first visual indication of the first abrasiveness and the second portion may include a second visual indication of the second abrasiveness. The deformable portion may be configured such that the abrasive outer surface and the deformable portion deform upon application of pressure during use of the drum assembly on a nail of a user. The deformable portion may include a first portion having a first hardness and a second portion having a second hardness different from the first portion. The drum assembly may be a first exchangeable drum assembly configured for removable and/or replaceable attachment to a cosmetic device, and may include at least one second exchangeable drum assembly configured for removable and/or replaceable attachment to the cosmetic device. The second exchangeable drum assembly may differ from the first exchangeable drum assembly in abrasiveness. The second exchangeable drum assembly may differ from the first exchangeable drum assembly in compressibility. The second exchangeable drum assembly may differ from the first exchangeable drum assembly in diameter. The second exchangeable drum assembly may differ from the first exchangeable drum assembly in thickness of the deformable portions. The second exchangeable drum assembly may include a plurality of exchangeable drum assemblies.

Another embodiment relates an adapter assembly for a cosmetic device. The adapter assembly includes an adapter body configured to be received within the cosmetic device, a first end configured to engage a first drive member of the cosmetic device, and a second drive member configured to engage a drum assembly. Rotation of the first drive member of the cosmetic device causes a corresponding rotation of the second drive member and the drum assembly. The adapter body may be a generally cylindrical member and may include an inner portion configured to rotate with the first drive member and an outer portion configured to remain stationary during rotation of the first drive member. The adapter assembly may include the drum assembly, wherein the drum assembly may include a plurality of drum members. The drum members may differ from each other in at least one of size, shape, compressibility, and abrasiveness. The drum members may be slidably received on a shaft. The shaft may be shaped to prevent relative rotation between the drum members and the shaft. The shaft may be triangular.

Another embodiment relates to a kit of drum assemblies. The kit may include a plurality of abrasive and compressible drum assemblies, each drum assembly configured to be rotated by a drive system of a cosmetic device. The drum assemblies may differ from each other in at least one of size, shape, abrasiveness, and compressibility.

Another embodiment relates to a cosmetic device. The cosmetic device includes a housing, an electromechanical drive system disposed at least partially within the housing, and a plurality of interchangeable drum assemblies, including at least a first drum assembly different from a second drum assembly. The first and second drum assemblies may be different in at least one of a shape, an abrasiveness, and a compressibility. The first and second drum assemblies may be different colors. The first and second drum assemblies may be configured for lateral insertion into the housing to engage a drive shaft of the electromechanical drive system.

Another embodiment relates to a cosmetic device. The cosmetic device includes an axially extending body defining an outer periphery in a circumferential direction and having: a first end, a second end axially opposite the first end, and a first portion between the first end and the second end, the first portion defining a first receptacle configured to receive a battery. The cosmetic device further includes a shell removably coupled to the body, the shell having at least one sidewall extending around the outer periphery of the body to at least partially define a cavity configured to receive the body and extending axially from the first end to substantially beyond the first portion.

Another embodiment relates to a cosmetic device. The cosmetic device includes a motor and an axially extending body defining an outer periphery in a circumferential direction and having: a first end, a second end axially opposite the first end, a first portion between the first end and the second end, the first portion defining a first receptacle configured to receive a battery, and a second portion between the first portion and the second end, the second portion housing the motor. The cosmetic device further includes electrical contacts located in the first receptacle, the electrical contacts electrically coupled to the motor; a drive shaft having a proximal end operably coupled to the motor and a distal end extending through the second end of the body; a drum coupled to the distal end of the drive shaft; and a shell removably coupled to the body, the shell having at least one sidewall extending around the outer periphery of the body to at least partially define a cavity configured to receive the body and extending axially from the first end to substantially beyond the first portion. The first receptacle may be configured such that when the battery is placed in the first receptacle, the battery is within the outer periphery of the body. The body may define a second receptacle located radially opposite the first receptacle. The first receptacle and the second receptacle may be configured such that when batteries are located in the first receptacle and the second receptacle, a center of gravity of the batteries lies along an axis substantially collinear with the drive shaft. The cosmetic may include a locking assembly to secure the shell to the body. The locking assembly may include a member extending from the first end of the body, and a clasp coupled to the shell and configured to engage the member to secure the shell to the body. The shell may include an end wall and the at least one sidewall extends axially from the end wall, and the clasp may be slidably coupled to the end wall to selectively engage and disengage the member. The drum may include an abrasive surface. The shell may include an end wall located proximate the first end of the body when the shell is coupled to the body. The at least one sidewall may extend axially from the end wall, the at least one sidewall may extend seamlessly around the outer periphery of the body. The at least one sidewall may seamlessly joins the end wall. The cosmetic device may include an actuator mounted to the body and configured to control operation of the motor. The actuator is mounted to the body proximate the second end of the body. The at least one sidewall defines an opening opposite the end wall and the at least one sidewall defines a cutout that extend partially around the actuator when the shell is coupled to the body. The body may include a ridge extending circumferentially around the body proximate the second end, and wherein when the shell is coupled to the body the at least one sidewall may extend from the end wall proximate the first end to the ridge such that the body between the first end and the ridge is substantially enclosed with in the shell.

BRIEF DESCRIPTION OF THE DRAWINGS

FIG. 4 is a rear perspective view of a drive system for a drum assembly according to an exemplary embodiment.

FIG. 5 is a front perspective view of the drive system and a drum assembly of FIG. 4.

FIG. 6 is an exploded front view of the drive system and a drum assembly of FIG. 4.

FIG. 7 is a front view of the drive system and a drum assembly of FIG. 4.

FIG. 8 is a left side view of the drive system and a drum assembly of FIG. 4.

FIG. 12 is a top front perspective view of a cosmetic device, shown according to an exemplary embodiment.

FIG. 13 is a top front perspective view of the cosmetic device of FIG. 12 with the cover removed.

FIG. 14 is a top rear perspective view of the cosmetic device of FIG. 12 with the cover removed.

FIG. 15 is cross-section view of a portion of a drive system and drum assembly of the cosmetic device of FIG. 12.

FIGS. 21A-21I shows various drum assemblies usable with cosmetic devices according to one embodiment.

FIG. 22 shows a drum assembly according to an alternative embodiment.

FIG. 23 shows a number of drum assemblies according to one embodiment.

DETAILED DESCRIPTION

Referring to the figures generally, various embodiments disclosed herein relate to abrasive drum assemblies, and cosmetic devices that may utilize various drum assemblies. The drum assembly may include an outer abrasive surface or layer provided over an underlying deformable or compressible layer. As such, along with providing abrasive features, the drum assembly provides a relatively soft, deformable, or flexible surface that can conform to various surfaces, including fingernails, toenails, skin, etc.

Before discussing further details of the cosmetic device and/or the components thereof, it should be noted that references to "front," "back," "rear," "upward," "downward," "inner," "outer," "right," and "left" in this description are merely used to identify the various elements as they are oriented in the Figures. These terms are not meant to limit the element which they describe, as the various elements may be oriented differently in various applications.

It should further be noted that for purposes of this disclosure, the term "coupled" means the joining of two members directly or indirectly to one another. Such joining may be stationary in nature or moveable in nature and/or such joining may allow for the flow of fluids, electricity, electrical signals, or other types of signals or communication between the two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

Figure 1:
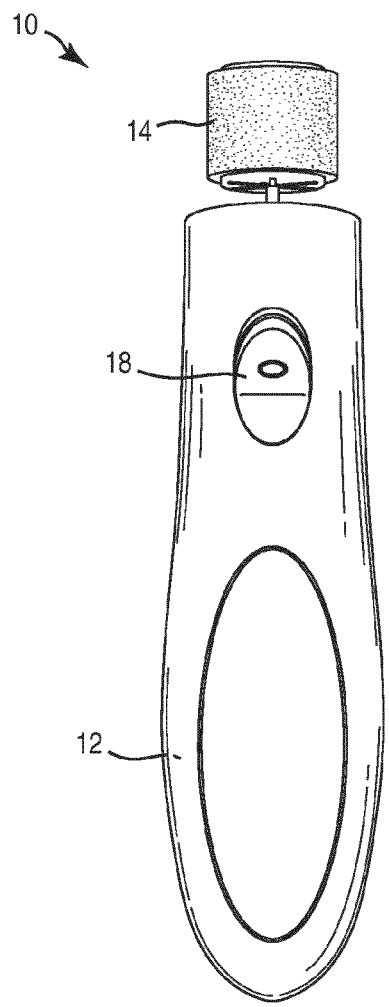
FIG. 1 is a front view of a cosmetic device, according to one embodiment.
Figure 2:
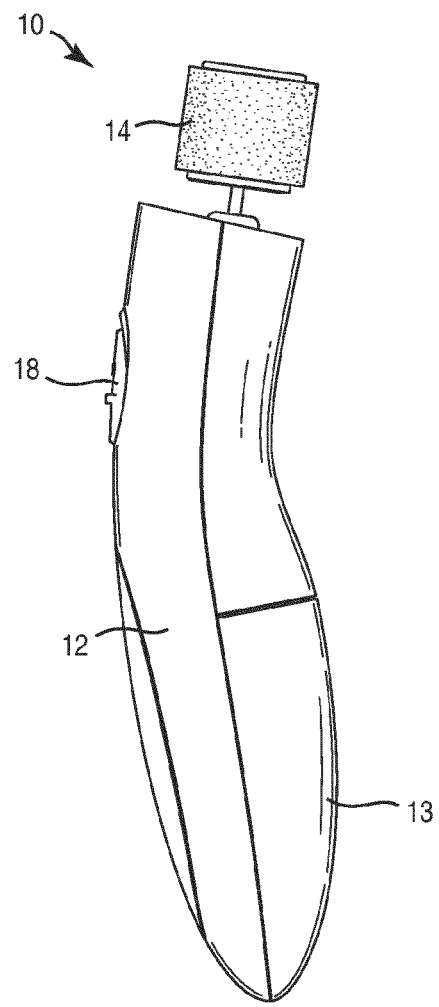
FIG. 2 is a right side view of the cosmetic device of FIG. 1.
Figure 3:
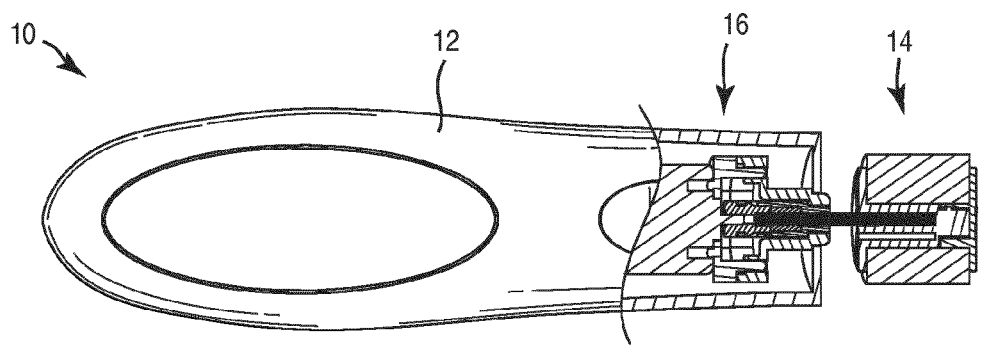
FIG. 3 is a broken view of the cosmetic device of FIG. 1 showing a drive system, according to an exemplary embodiment.

Referring to FIGS. 1-3, a cosmetic device 10 is shown according to one embodiment. Device 10 includes a housing 12 that supports a drum assembly 14. A drive system 16 is disposed within housing 12 and coupled to drum assembly 14. A control member 18 (e.g., a switch, button, lever, knob, etc.) is also disposed within housing 12 (e.g., extending though an aperture in the housing), and controls operation of drive system 16 and drum assembly 14.

Housing 12 is configured to contain or otherwise support various components of device 10. In some embodiments, housing 12 is configured as a handheld device and is shaped to be comfortable in a user's hand during use. As shown in the figures, housing 12 may take a variety of shapes, including cylindrical, curved, rounded, etc. In one embodiment, housing 12 is made of a polymer (e.g., plastic material). In other embodiments, housing 12 can be made of other materials including various composites, ceramics, or metal materials. One or more portions 13 of housing 12 can be removable to provide access to, for example, a battery compartment.

Referring to FIGS. 4-8, drum assembly 14 in one embodiment includes drum 30 and shaft 32. Drum 30 includes an outer surface or layer 34, an inner, resiliently deformable layer or portion 36, and core portions 35 and 37. Outer surface 34 and inner portion 36 define the outer shape, or periphery of drum 30. In one embodiment, drum 30 includes a cylindrical portion. In various embodiments, drum 30 includes a domed (e.g., semispherical, etc.) portion extending from an end of the cylindrical portion. In other embodiments, drum 30 includes a disc-shaped portion extending from or coupled to an end of the cylindrical portion.

According to various alternative embodiments, drum 30 can be any number of different sizes. For example, drum 30 may define a diameter, and the diameter may take a range of values. In one embodiment, the diameter of drum 30 is no more than about 1 inch (approximately 2.5 cm), no more than about 0.75 inches (approximately 1.9 cm), or no more than about 0.5 inches (approximately 1.3 cm). Similarly, drum 30 may define a length (e.g., running along a longitudinal axis of the drum), and the length may take a range of values. In one embodiment, the length is no more than about 1 inch (approximately 2.5 cm), no more than about 0.75 inches (approximately 1.9 cm), or no more than about 0.5 inches (approximately 1.3 cm). In a further embodiment, a cylindrical portion of drum 30 has a diameter of approximately 0.8 inches (approximately 2 cm) and a length of approximately 0.5 inches (approximately 1.3 cm). In another embodiment, a cylindrical portion of drum 30 has a diameter of approximately 0.95 inches (approximately 2.4 cm) and a length of approximately 0.8 inches 0.8 inches (approximately 2 cm). In other embodiments drum 30 may take other shapes and sizes.

In one embodiment, outer layer 34 provides an abrasive material configured to remove material from a fingernail, toenail, callous, or other surface in order to smooth and/or shine the surface. Outer layer 34 and the abrasive material can be provided in a variety of ways. For example, in one embodiment, outer layer 34 is provided in the form of a sheet of material (e.g., sandpaper, etc.) having a substrate and an abrasive layer provided on the substrate. The abrasive coating can be sprayed or brushed on to the substrate, adhered to the substrate, or applied in another suitable fashion. In another embodiment, inner portion 36 can act as a substrate for the abrasive material, such that an abrasive material (e.g., sand, stones, diamonds, etc.) can be adhered or otherwise applied directly to inner portion 36. In another embodiment, the abrasive material may be distributed evenly throughout inner portion 36, such that an abrasive material is exposed to the outer surface of inner portion 36 as inner portion 36 is worn down through use of drum assembly 14.

The abrasive material can take many different forms, including synthetic or naturally occurring stone materials, microstones, diamonds, crystals, etc., and be provided with varying degrees of abrasiveness (e.g., roughness). In one embodiment, outer layer 34 is provided in the form of a sheet of material having approximately 500 particles per square inch. In other embodiments, outer layer 34 has approximately 1000 particles per square inch. In yet further embodiments, other levels of abrasiveness may be used for outer layer 34 can be used to achieve a desired effect or provide a desired appearance for a nail, skin, etc. For example, outer layer 34 may be relatively coarse (e.g., less than P400) for shaping a nail, may be relatively fine (e.g., between P400 and P800) for buffing, or may be very fine (e.g., greater than P2000) for polishing. In other embodiments, outer layer 34 may have any suitable particle density and size.

Inner portion 36 can also take a variety of forms. In one embodiment, inner portion 36 includes a foam material (e.g., a solid foam material) configured to enable outer layer 34 to resiliently deform or compress during use of device 10. For example, inner portion 36 can be configured such that during use of device 10, outer layer 34 can generally conform to the shape of a nail, skin, etc. Furthermore, the hardness (e.g., compressibility, deformability, flexibility, etc.) of inner portion 36 can be varied, from being a relatively compliant, deformable, or flexible material, to being a relatively stiff and less flexible material. Any suitable material can be used to form inner portion 36, including a variety of polymers (e.g., rubber, polyethylene, etc.) and other materials.

Figure 9:
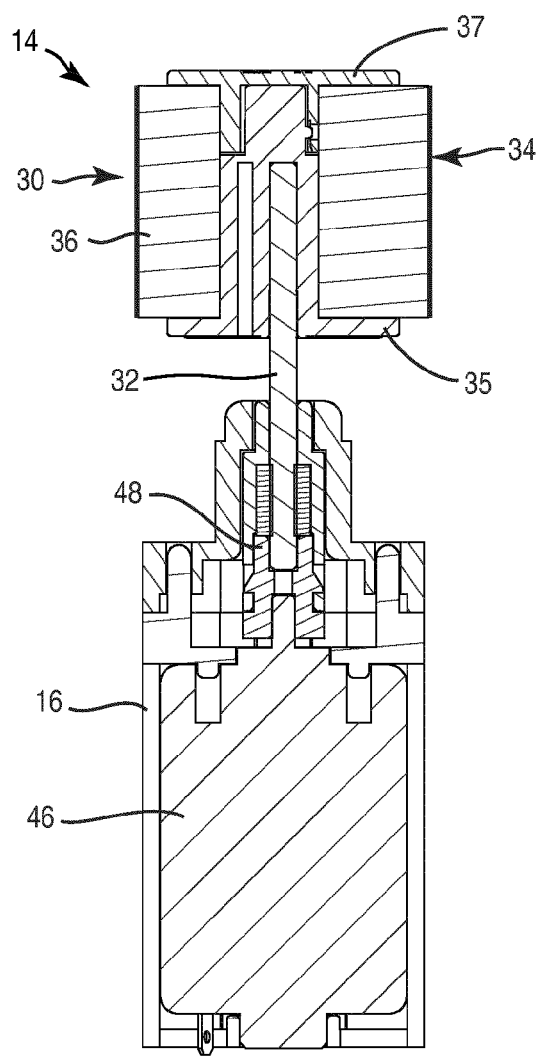
FIG. 9 is a cross-section view of a portion of a drive system and drum assembly of FIG. 8, taken along line 9-9.

Referring to FIG. 9, according to one embodiment, drive system 16 includes a chuck or drive member 48 configured to engage shaft 32 of drum assembly 14. Drive member 48 is configured to be driven, or rotated, by drive mechanism 46 (e.g., an electric motor) during operation of device 10. In one exemplary embodiment, drive mechanism 48 rotates drum assembly 14 between approximately 100 rpm and 20,000 rpm. Drive member 48 includes a recess configured to receive a portion of shaft 32 in a rotatably fixed manner such that rotation of drive member 48 causes a corresponding rotation of shaft 32 and drum assembly 14. In one embodiment, drive member 48 and shaft 32 include corresponding geometric features (e.g., splines, keys, etc.) configured to prevent relative rotation between the components. Although FIG. 9 shows shaft 32 being received in a recess formed in drive member 48, it should be understood that according to other embodiments, drive member 48 can be received in a recess formed in shaft 32. Furthermore, other types of couplings can be used according to various other alternative embodiments (e.g., meshing gears, belt drive systems, etc.).

Figure 10:
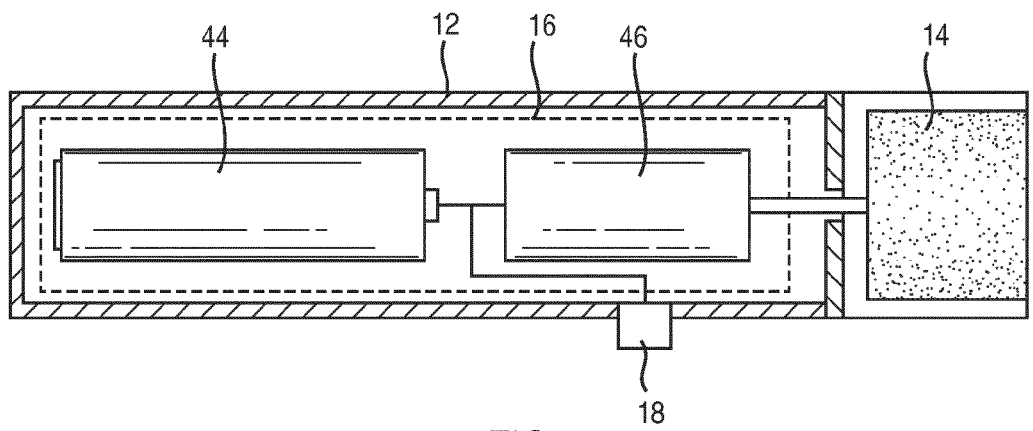
FIG. 10 is a schematic illustration of a portion of a cosmetic device according to one embodiment.

Referring now to FIG. 10, a schematic illustration of device 10 is shown according to one embodiment. As shown in FIG. 10, device 10 includes drum assembly 14 coupled to drive system 16. Control member 18 controls operation of drive system 16 (and therefore drum assembly 14). Drive system 16 in one embodiment includes power source 44 and drive mechanism 46. In one embodiment, power source 44 is a battery and drive mechanism 46 is an electric motor configured to be powered by the battery. The battery can be replaceable and/or rechargeable. In other embodiments, power source 44 can include a power cord or similar device configured to provide power from a wall outlet or other exterior source to drive mechanism 46. According to various other embodiments, other types of power sources or drive mechanisms can be used in connection with drive system 16.

According to one embodiment, control member 18 is a button, switch, or similar device configured to control operation of drive system 16. Control member 18 controls on/off functionality for drive system 16. In some embodiments, control member can further provide speed control features for a user to control the rotational speed of drum assembly 14. For example, control member can be moveable between a discreet number of positions, with each position corresponding to a different speed for the drum assembly (e.g., off, low speed, high speed, etc.). In other embodiments, control member 18 can be infinitely adjustable between upper and lower speed extremes (e.g., rather than adjustable only between predetermined speeds).

In one embodiment, control member 18 can extend through an aperture in housing 12, and be configured to slide, rotate, etc. to control the operation of drive system 16. In other embodiments, control member 18 can be provided as part of or integrated into housing 12 (e.g., as a slidable, rotatable, or otherwise moveable portion of the housing).

Figure 11:
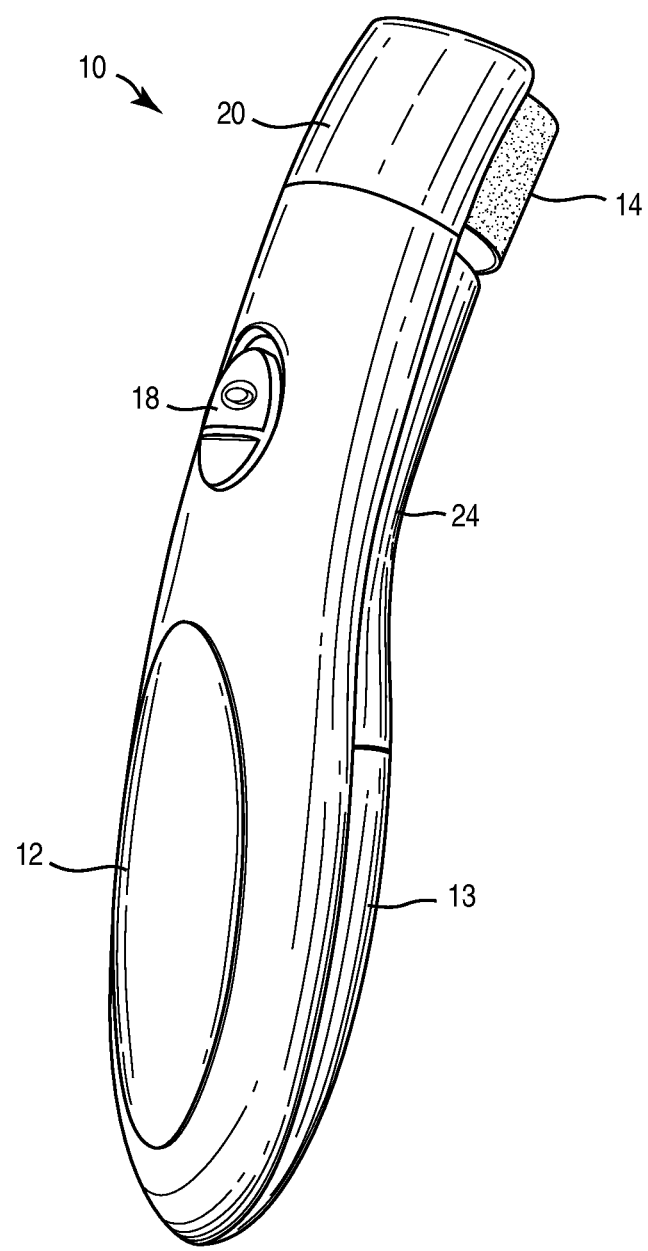
FIG. 11 is a perspective view of the cosmetic device of FIG. 1 including a guard partially surrounding the drum assembly.

Referring to FIG. 11, in one embodiment shield or guard 20 may be coupled to housing 12 and extend about a portion of drum assembly 14. Guard 20 extends from housing 12 in a relatively smooth manner, such that the transitional area between housing 12 and guard 20 forms a generally continuous surface (e.g., a continuous, contoured surface, etc.). Furthermore, as discussed in greater detail below, device 10 is, in some embodiments, provided as part of a kit including multiple drum assemblies having the same or different abrasiveness, compressibility, shape, or size.

Referring in general to FIGS. 12-18, a cosmetic device 110 is shown according to another embodiment. The device 110 includes a housing 112 that supports a drum assembly 114. A drive system 116 (see FIG. 15) is disposed within the housing 112 and coupled to the drum assembly 114. An actuator 118 (e.g., a switch, button, lever, knob, control member, etc.) is also disposed within the housing 112 (e.g., extending though an aperture in the housing 112), and controls operation of the drive system 116 and the drum assembly 114.

The housing 112 is configured to contain or otherwise support various components of the device 110. In some embodiments, the housing 112 is configured as a handheld device and is shaped to be comfortable in a user's hand during use. As shown in the figures, in one embodiment, the housing 112 may have a generally rectangular cross-sectional shape. The housing 112 may have rounded edges to improve the ergonomics of the cosmetic device 110 and make it more comfortable for a user to hold. In one embodiment, the housing 112 is made of a polymer (e.g., plastic material). In other embodiments, the housing 112 can be made of other materials including various composites or metal materials. One or more portions of the housing 112 can be removable to provide access to, for example, a battery compartment provided within the housing 112. As shown in FIG. 15, the housing 112 may include an inner portion, shown as a body 120, that is received within an outer portion, shown as a shell 122. The body 120 may be substantially concealed within the shell 122 and the shell 122 may be configured to have a relatively smooth outer surface that is free of seams, part lines, or other features. Part lines around the periphery of the shell 122 may degrade from the aesthetic of the shell and/or may irritate a user's hand during long periods of use.

In one embodiment a guard or shield 124 may be coupled to the housing 112 and extend about a portion of the drum assembly 114. The shield 124 extends from the housing 112 in a relatively smooth manner, such that the transitional area between the housing 112 and the shield 124 forms a generally continuous surface (e.g., a continuous, contoured surface, etc.). In one embodiment, the device 110 includes a cap 126 that is configured to be removably coupled to the housing 112 to protect and/or conceal the drum assembly 114 between periods of use. In one embodiment, the cap 126 may include a cutout 128 through which a portion 125 of the shield 124 and/or the housing 112 may protrude through the cap 126. The protruding portion 125 may be configured to form a generally continuous (e.g., substantially flush) surface with the cap 126. According to an exemplary embodiment, the cap 126 may include an internal feature (e.g., a slot, depression, detent, ridge, etc.) that engages a ridge 127 extending outward from the housing 112. The cap 126 may be coupled to the housing by pressing the cap 126 against the housing until the internal feature of the cap 126 engages the ridge 127. According to another embodiment, the cap may include a ridge and the housing may define a slot configured to detentedly receive the ridge.

Referring further to FIGS. 15-18, the drum assembly 114 in one embodiment is a removable body. The drum assembly 114 includes a drum 130 and a shaft 132 (e.g., drive shaft, etc.). The drum 130 includes an outer surface or layer 134 and an inner portion. In one embodiment, drum 130 is a generally cylindrical body. In alternative embodiments, the drum 130 may be otherwise shaped (e.g., domed, conical, semispherical, etc.). The outer layer 134 may provide an abrasive material configured to remove material from a fingernail, toenail, or other surface in order to smooth and/or shine the surface. The outer layer 134 and the abrasive material can be provided in a variety of ways. For example, in one embodiment, the outer layer 134 is provided in the form of a sheet of material (e.g., sandpaper, etc.) having a substrate and an abrasive layer provided on the substrate. The abrasive coating can be sprayed or brushed on to the substrate, adhered to the substrate, or applied in another suitable fashion. In another embodiment, the inner portion of the drum 130 can act as a substrate for the abrasive material, such that an abrasive material (e.g., stones, diamonds, etc.) can be adhered or otherwise applied directly to inner portion of the drum 130. In another embodiment, the abrasive material may be distributed evenly throughout the inner portion of the drum, such that an abrasive material is exposed to the outer surface of the inner portion of the drum 130 as the drum is worn down through use of drum assembly 114.

Referring to FIG. 15, a schematic illustration of the device 110 is shown according to one embodiment. According to one embodiment, the drive system 116 includes a drive member 148 (e.g., chuck) configured to engage the shaft 132 of the drum assembly 114. The drive member 148 is configured to be driven, or rotated, by a drive mechanism, shown as an electric motor 146 during operation of the device 110. In one exemplary embodiment, the motor 146 rotates the drum assembly 114 between approximately 1100 rpm and 120,000 rpm. In one embodiment, the shaft 132 of the drum assembly 114 is positioned along a longitudinal axis 129 of the device 110. The drive member 148 includes a recess configured to receive a portion of the shaft 132 in a rotatably fixed manner such that rotation of the drive member 148 causes a corresponding rotation of the shaft 132 and the drum assembly 114. In one embodiment, the drive member 148 and the shaft 132 include corresponding geometric features (e.g., splines, keys, etc.) configured to prevent relative rotation between the components. While FIG. 9 shows shaft 132 being received in a recess formed in drive member 148, it should be understood that according to other embodiments, drive member 148 can be received in a recess formed in shaft 132. Furthermore, other types of couplings can be used according to various other alternative embodiments (e.g., meshing gears, belt drive systems, etc.).

The shaft 132 may have any suitable cross-sectional shape. According to one embodiment, at least a portion 138 of the shaft 132 has a generally triangular cross-section that extends through an aperture 136 in the drum 130 (see, e.g., FIG. 27). The aperture 136 is shown to have a generally triangular cross-section. According to an exemplary embodiment, the drum 130 may be removably mounted on the portion 138 of the shaft.

In other embodiments, the drum assembly 114 may be permanently coupled to the drive system 116. The drive system 116 may lack a drive member 148. Instead, the shaft 132 may be formed by an output shaft of the motor 146 that extend out of the interior of the housing 112 through an opening 142 formed in an end of the housing 112.

As shown in FIG. 15, the device 110 includes the drum assembly 114 coupled to the drive system 116. The actuator 118 controls operation of the drive system 116 (and therefore the drum assembly 114). The drive system 116 in one embodiment includes a power source, shown as a battery 144 and the motor 146. The battery 144 can be replaceable and/or rechargeable. In other embodiments, the power source can include a power cord or similar device configured to provide power from a wall outlet or other exterior source to the motor 146. According to various other embodiments, other types of power sources or drive mechanisms can be used in connection with the drive system 116.

According to one embodiment, the actuator 118 is a button, switch, or similar device configured to control operation of the drive system 116. The actuator 118 controls the on/off functionality for the drive system 116. In some embodiments, the actuator 118 can further provide speed control features for a user to control the rotational speed of the drum assembly 114. For example, the actuator 118 can be moveable between a discreet number of positions, with each position corresponding to a different speed for the drum assembly (e.g., off, low speed, high speed, etc.). In other embodiments, the actuator 118 can be infinitely adjustable between upper and lower speed extremes (e.g., rather than adjustable only between predetermined speeds). In one embodiment, the actuator 118 can extend through an aperture in the housing 112, and be configured to slide, rotate, etc. to control the operation of the drive system 116. In other embodiments, the actuator 118 can be provided as part of or integrated into the housing 112 (e.g., as a slidable, rotatable, or otherwise moveable portion of the housing).

Figure 16:
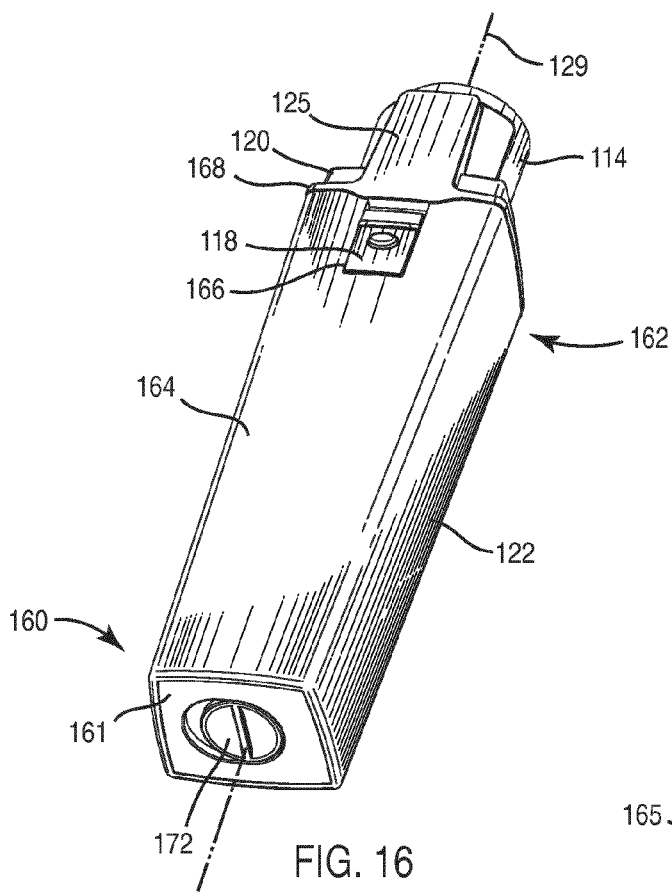
FIG. 16 is a bottom front perspective view of the cosmetic device of FIG. 12.
Figure 17:
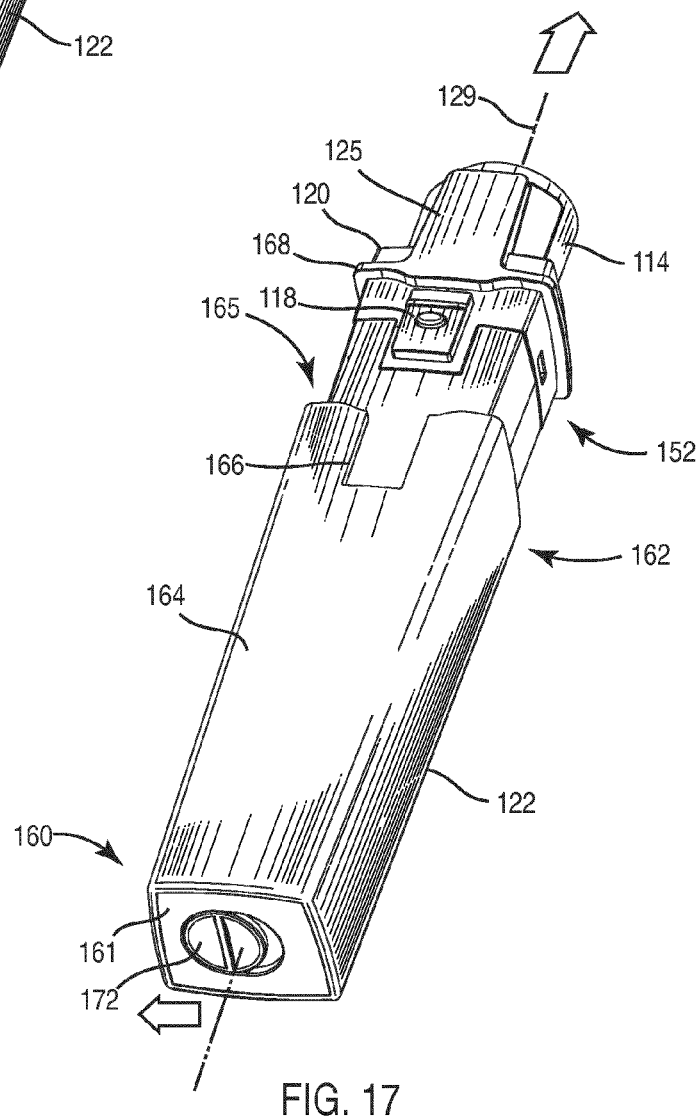
FIG. 17 is a bottom front perspective view of the cosmetic device of FIG. 12 with the shell disengaged from the body and the body partially removed from the shell.
Figure 18:
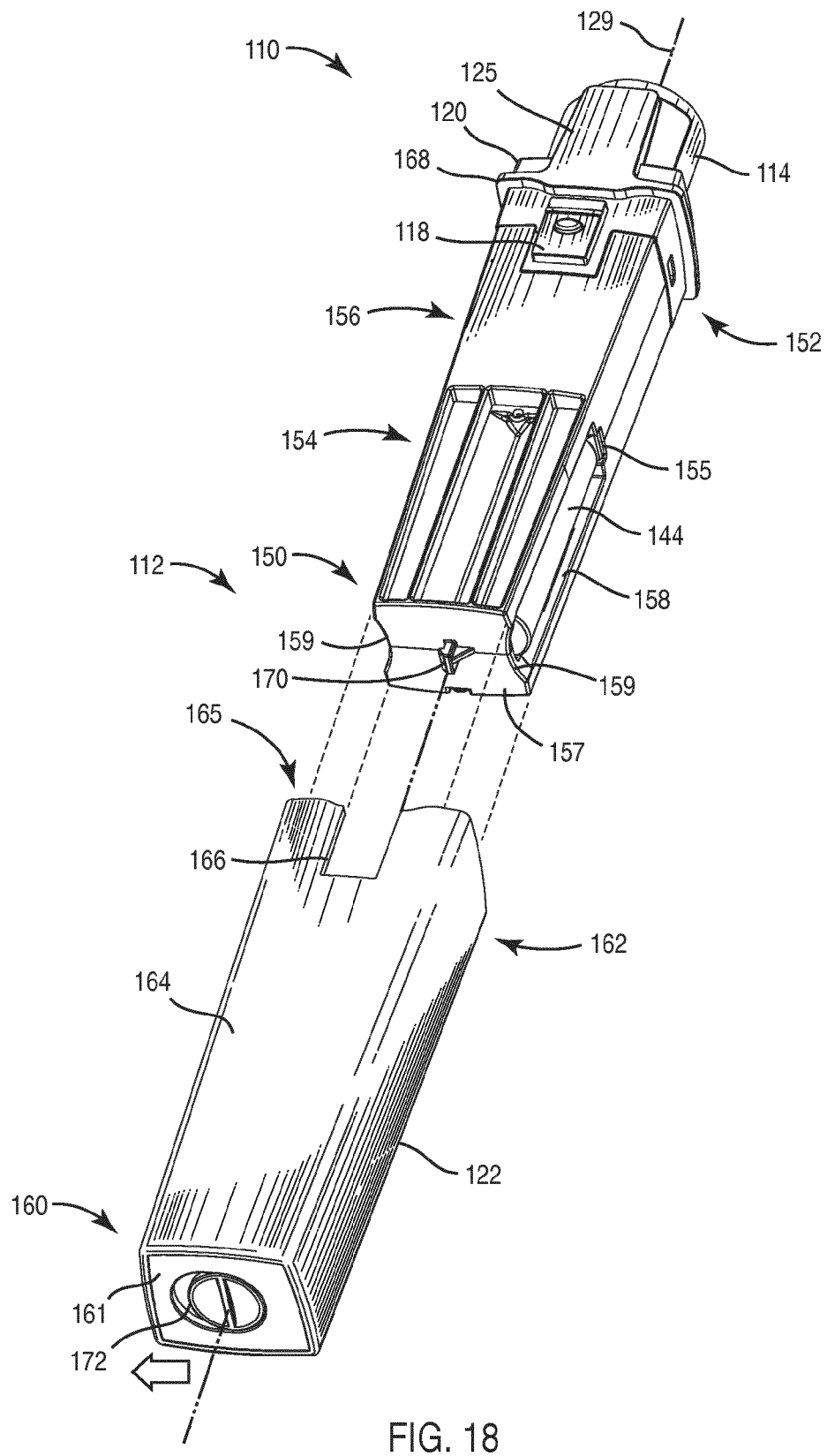
FIG. 18 is an exploded perspective view of the cosmetic device of FIG. 12.

Referring now to FIGS. 16-18, the housing 112 is shown in more detail including the body 120 nested within the shell 122. The body 120 provides a structure to which the drive system 116 is mounted. The body 120 is an elongated member that extends along the longitudinal axis 129. The body 120 includes a first end 150 and a second end 152 opposite the first end. A first portion 154 of the body 120 is configured to receive one or more batteries 144. A second portion 156 of the body 120 is configured to receive the motor 146.

The first portion 154 is positioned proximate the first end 150 of the body 120. The first portion 154 defines one or more receptacles 158 into which the battery 144 may be inserted. When in the receptacle 158, the battery 144 is contained entirely within the body 120 such that it does not protrude beyond the outer periphery of the body 120. Electrical contacts 155 are located in the receptacle 158 and are positioned such that the terminals of the battery 144 are in contact with the electrical contacts 155 when the battery 144 is received in the receptacle 158 such that the battery is electrically coupled to the motor 146 through the electrical contacts 155. According to an exemplary embodiment, an end wall 157 of the body 120 may include cutouts 159. The cutouts 159 extend into the receptacles 158 such that a user may grasp or otherwise manipulate the battery 144 received in the receptacle 158 through the cutout 159, thereby facilitating the removal of the battery 144 from the receptacle 158 (e.g., when replacing the battery 144).

According to one exemplary embodiment, the first portion 154 is configured to receive two batteries 144 in receptacles 158 provided on opposite sides of the body 120. The receptacles 158 are arranged such that batteries 144 are arranged generally symmetrically about the longitudinal axis 129. In this arrangement, the batteries 144 do not substantially shift the center of mass of the device 110, which may, in one embodiment, be substantially collinear or coaxial with the longitudinal axis 129. Keeping the center of gravity coincident with the longitudinal axis 129 improves the feel of the device in the user's hand.

The second portion 156 is a generally closed body in which the motor 146 is mounted. The second portion 156 is positioned between the first portion 154 and the second end 152. The output shaft of the motor 146 extends away from the first portion 154 towards the second end 152. In one embodiment, the output shaft of the motor 146 extends out of the opening 142 formed in the second end 152 and the distal end of the output shaft is coupled to the drum 130. In another embodiment, a shaft 132 coupled to the drum 130 extends into the interior of the second portion 156 and is rotationally coupled to the output shaft of the motor 146 (e.g., with the drive member 148).

The shell 122 is a hollow, thin-walled body with a closed first end 160 formed by an end wall 161, an open second end 162, and one or more side walls 164 extending between the first end 160 and the second end 162. The shell 122 may be tapered and may have a circumference (e.g., the sum of the widths of the one or more side walls 164) at the second end 162 that is greater than the circumference at the first end 160. A cutout 166 may be formed in one of the side walls 164 that opens into the second end 162. The actuator 118, which is positioned proximate the second end 152 of the body 120, is received in the cutout 166 when the shell 122 is coupled to the body 120. The actuator 118 may extend beyond the outer surface of the shell 122, allowing a user to tactilely locate and operate the actuator 118 while still maintaining a relatively smooth, uninterrupted outer contour of the device 110.

The body 120 may include an outwardly extending flange or ridge 168 proximate the second end 152. When the shell 122 is coupled to the body 120 the ridge 168 abuts the edges of the side walls 164 and the portion of the body 120 between the first end 150 and the ridge 168 is substantially enclosed within the shell 122. The ridge 168 may extend away from the body 120 by a distance generally equal to the thickness of the side walls 164, such that the shell 122, the ridge 168, and the cap 126 form a substantially smooth, continuous contour when the body 120 is coupled to the shell 122 and the cap 126 is coupled to the housing 112.

The shell 122 defines an interior volume or cavity 165 configured to receive the body 120. The body 120 is received and nests snugly in the shell 122 (e.g., without excess "play" or space between the body 120 and the shell 122). According to an exemplary embodiment, the body 120 and the shell 122 each have a generally rectangular cross-section. In other exemplary embodiments, the body 120 and the shell 122 may by similarly shaped with another cross-section (e.g., circular, oval, hexagonal, etc.). Having similar cross-sections facilitates the sliding of the body 120 relative to the shell 122 between a first position, in which the body 120 is coupled to the shell 122 and is concealed within the shell 122 and a second position, in which the body 120 is slid along the longitudinal axis 129 away from the shell 122 to expose the first portion 154 and the second portion 156 (e.g., to replace the batteries 144). In the first position, when the body 120 is coupled to the shell 122, the shell 122 encloses the body 120 and protects the drive system 116 (e.g., from water, undesirable debris, inadvertent contact, etc.).

The body 120 is coupled to the shell 122 with a locking assembly that is engaged when the body 120 is in the first position, seated within the shell 122. According to an exemplary embodiment, the locking assembly includes a member 170 extending from the first end 150 of the body 120 and a sliding member 172, having an internal clasp. The sliding member 172 is coupled to the end wall 161 of the shell 122 and is configured to engage the member 170 to secure the shell 122 to the body 120. According to an exemplary embodiment, the sliding member 172 is biased such that it automatically engages the member 170 when the body 120 is seated within the shell 122. A user may manually slide the sliding member 172 to disengage the clasp from the member 170 and allow the body 120 to be slid out of the shell 122. According to an exemplary embodiment, the sliding member 172 is coupled to the end wall 161 such that it is positioned away from the side walls 160 and does not interrupt the relatively smooth outer contour of the device 110. In other embodiments, the sliding member 172 may be coupled to one of the side walls 160 and the member 170 may extend from a side of the body 120. In other embodiments, the body 120 may be coupled to the shell 122 with another mechanism, such as with a ridge extending from the body 120 or the shell engaging a corresponding detent formed in the other component. According to one embodiment, one or more springs may be located on the inside of the end wall 161. When the body 120 is seated within the shell 122, the spring is compressed. Thus, when the locking assembly is released (e.g., the clasp and the member 170 disengage, etc.) the body 120 is pushed out of the shell 122.

Figures 19, 20:
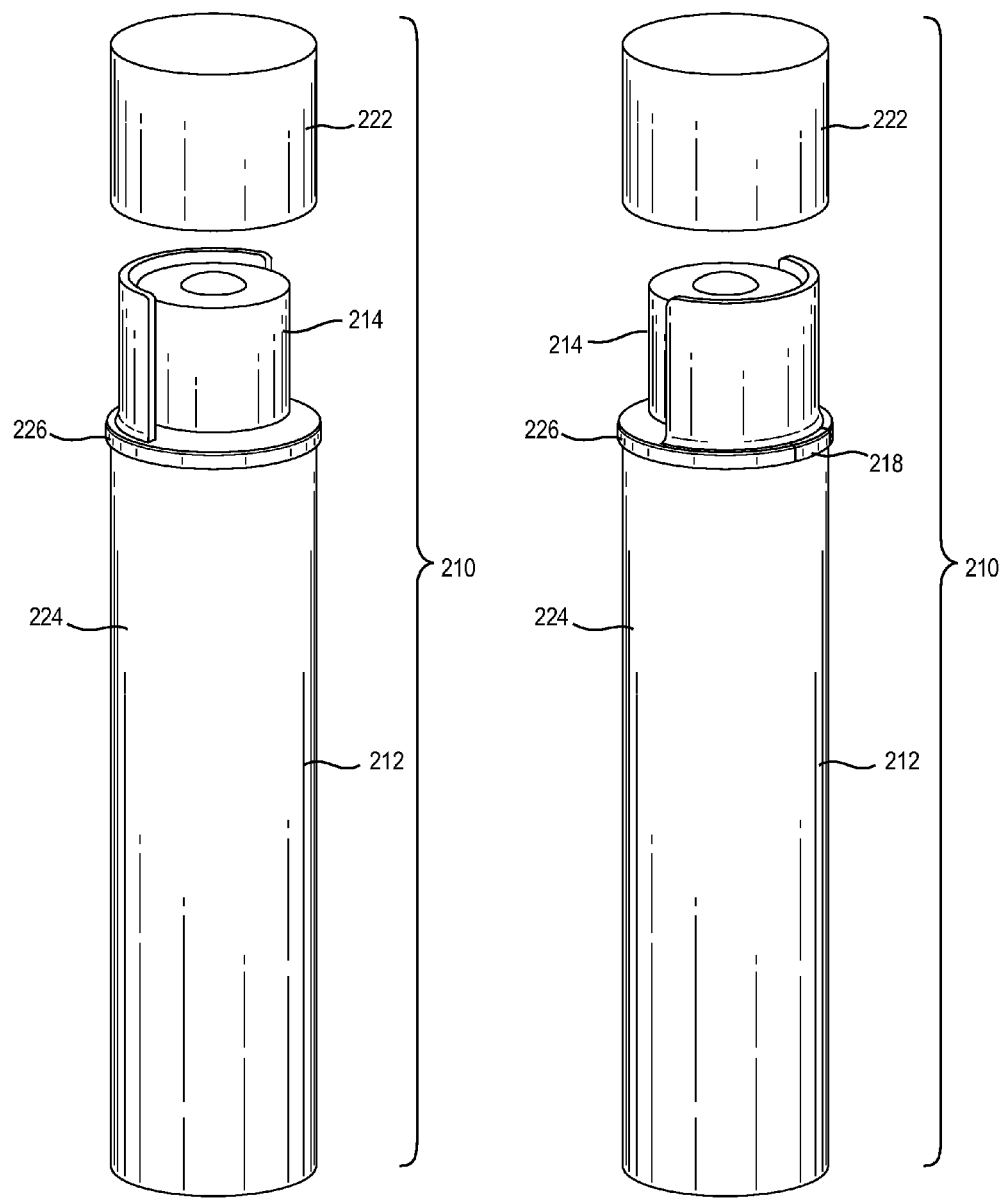
FIG. 19 is an exploded top front perspective view of a cosmetic device, shown according to an exemplary embodiment.
FIG. 20 is an exploded top rear perspective view of the cosmetic device of FIG. 19.

Referring to FIGS. 19-20, a cosmetic device 210 is shown according to an alternative embodiment. Device 210 provides similar functionality to device 110, and can include any or all of the features described with respect to device 110 and FIGS. 12-18. Device 210 includes a cover 222 that is configured to be removably coupled to housing 212 to protect and/or conceal drum assembly 214 between periods of use. In one embodiment, housing 212 includes a lower portion 224 and an upper portion 226. Lower portion 224 is a generally cylindrical member having a first closed end and a second open end defining an interior configured to house various components such as a drive system, etc. Upper portion 226 is coupled to the open end of lower portion 224 to close the interior of housing 212 and protect the components therein (e.g., from water, undesirable debris, etc.).

In one embodiment, control member 218 is integrated into housing 212. For example, upper portion 226 of housing 212 can be rotatable relative lower portion 224 of housing 212 to provide switching functions for device 210 (e.g., on/off, speed control, etc.). Other types of control members can be utilized according to various other embodiments. Upper portion 226 can also be removable to provide access to a drive system (e.g., motor, battery) and other components.

Referring now to FIGS. 21A-21I, various embodiments of a drum assembly are shown according to alternative embodiments. As shown in FIG. 21A, drum assembly 314 can in one embodiment include a generally cylindrical portion 340 and a generally domed (e.g., semispherical, etc.) portion 342 extending from an end of the cylindrical portion 340. In other embodiments, drum 30 includes a disc-shaped portion 345 extending from or coupled to an end of the cylindrical portion.

In some embodiments, as shown in FIG. 21A, the domed portion can have a relatively large radius of curvature. In other embodiments, as shown in FIG. 21B, the domed portion can have a conical section, or a conical-like section, terminating at a relative smaller domed portion with a relatively smaller radius of curvature. In yet further embodiments, as shown in FIG. 21C, rather than a domed portion, drum assembly 314 can include a relative flat, or disc-shaped portion 345 on one end of drum assembly 314.

As shown in FIG. 21D, drum assembly 314 can in one embodiment be a frustoconical body that is tapered towards the distal end (e.g., the end remote from the drive mechanism 46). As shown in FIG. 21E, drum assembly 314 can in one embodiment be a frustoconical body that is tapered towards the proximal end (e.g., the end proximate to the drive mechanism 46). As shown in FIG. 21F, drum assembly 314 can in one embodiment be a conical body. As shown in FIG. 21G, drum assembly 314 can in one embodiment be a generally spherical body. As shown in FIG. 21H, drum assembly 314 can in one embodiment be an ellipsoid. As shown in FIG. 21I, drum assembly can in one embodiment be a paraboloid. Other shapes and sizes for drum assembly 314 are possible according to various alternative embodiments.

Referring now to FIG. 22, drum assembly 414 is shown according to an alternative embodiment. Drum assembly 414 is similar in many respects to drum assembly 314, and includes an outer layer 434 and an inner, or deformable portion 436. Drum assembly 414 further includes a first drum portion 420 and a second drum portion 422. First and second portions 420, 422 provide different characteristics for a user. In one embodiment, first and second portions 420, 422 have different abrasive characteristics, such as different types of abrasives, different levels of abrasiveness, etc. For example, first portion 420 may provide a relatively more abrasive surface and second portion 422 may provide a relatively less abrasive surface. In some embodiments, first and second portions 420, 422 can be provided with a visual indication such as a color, a stripe, etc. to provide an indication of the type of abrasive, degree of abrasiveness, etc.

In another embodiment, first and second portions 420, 422 have different hardnesses (e.g., differing characteristics regarding compressibility, deformation, flexibility, etc.). For example, first portion 420 may provide a relatively harder, and less flexible or deformable abrasive surface, and second portion 422 may provide a relatively softer, or more flexible or deformable abrasive surface. In some embodiments, first and second portions 420, 422 can be provided with a visual indication such as a color, a stripe, etc. to provide an indication of relative hardness, deformability, or flexibility of the abrasive material. While first and second portions 420, 422 are shown in FIG. 16 as being generally cylindrical, in other embodiments, first and second portions 420, 422 can take other shapes, including domed (e.g., semispherical, etc.), disc-shaped, etc.

Referring now to FIG. 23, in some embodiments, one or more additional drum assemblies can be provided separately or along with a cosmetic device such as device 10 to provide drum assembly options to users in terms of drum size, compressibility, abrasive characteristics, etc. For example, as shown in FIG. 23, drum assemblies 514, 614, and 714 can be provided as a kit (either separate from or with a device such as device 10). In one embodiment, drum assemblies 514, 614, and 714 are the same in size, shape, and abrasive characteristics, and are provided so that a user can replace drum assemblies as the drum assemblies become worn, etc.

In another embodiment, drum assemblies 514, 614, and 714 differ in at least one characteristic. The drum assemblies can differ in size (e.g., diameter, length, etc.), shape (to provide configurations such as those shown in FIGS. 21A-21C), type of abrasive, level of abrasiveness, etc. Differences between drum assemblies can be indicated by use of a visual indication such as a color of the drum assembly, a marking on the drum assembly, etc.). Further, one or more drum assemblies, such as drum assembly 714, can have different portions that provide different characteristics, including any of the characteristics discussed elsewhere herein (e.g., abrasiveness, shape, compressibility, etc.).

Figure 24:
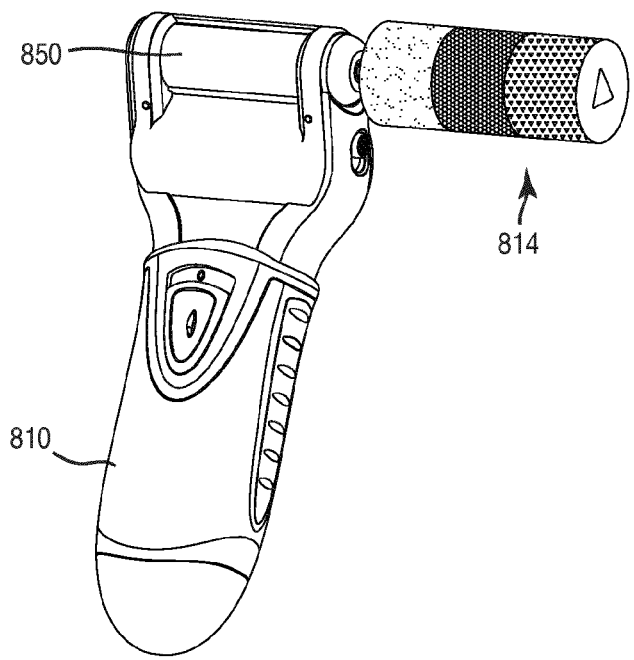
FIG. 24 is a perspective view of a drum assembly coupled to a cosmetic device by way of an adapter assembly, according to one embodiment.
Figure 25:
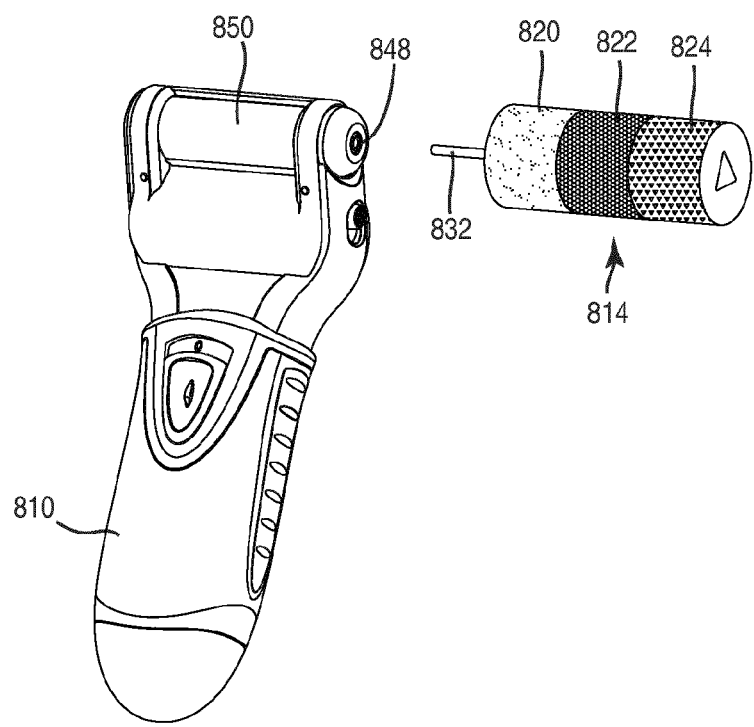
FIG. 25 is an exploded perspective view of the drum assembly and cosmetic device of FIG. 24.
Figure 26:
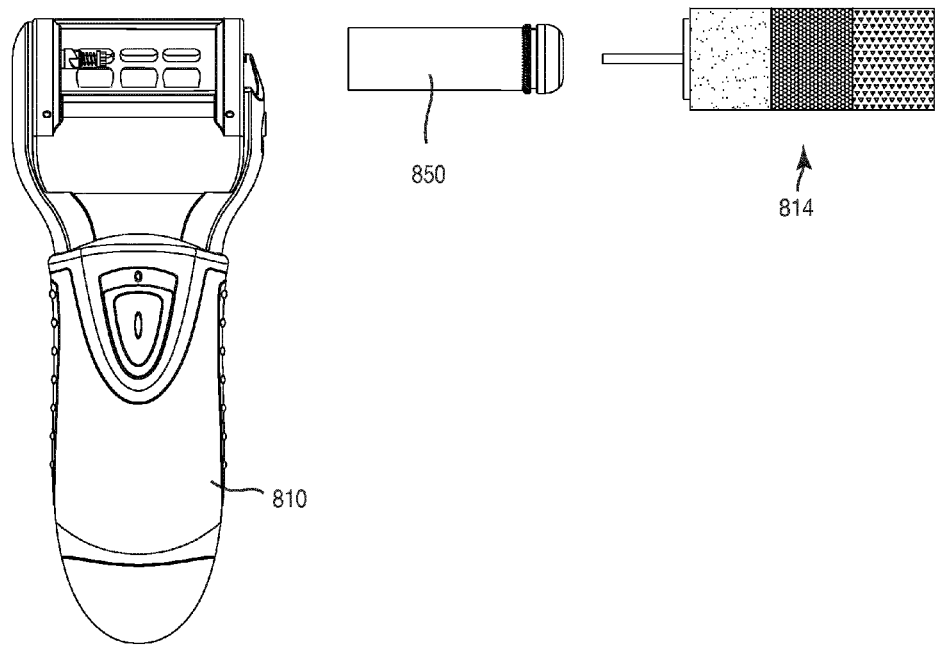
FIG. 26 is an exploded front view of the drum assembly and cosmetic device of FIG. 24.

Referring now to FIGS. 24-26, in some embodiments, a drum assembly 814 is usable with other devices such as device 810 by way of an adapter assembly 850. Device 810 is configured to receive a roller or similar component such that during operation of device 810, the roller rotates to abrade skin, etc. As shown in FIG. 24, in some embodiments, the roller can be provided in the form of adapter assembly 850 and be configured to be coupled to drum assembly 814. Adapter assembly 850 includes a first end configured to engage a first drive member of device 810, and a second drive member configured to engage the drum assembly. An inner portion of adapter assembly 850 may be rotatable with the drive members while an outer portion remains stationary. Any suitable coupling mechanism can be used to couple drum assembly 814 to adapter assembly 850, such as that shown in FIG. 3 or another suitable coupling feature. As shown in FIG. 25, a drive member 848 includes a recess configured to receive a portion of a shaft 832 in a rotatably fixed manner such that rotation of drive member 848 causes a corresponding rotation of shaft 832 and drum assembly 814. Adapter assembly 850 and drum assembly 814 are configured such that once assembled, drum assembly will extend from a lateral side of device 810. As such, adapter assembly 850 and drum assembly 814 can be removed laterally from the device while a drive shaft or similar member remains coupled to the device.

As can be seen in FIGS. 24-26, drum assembly 814 may be usable with preexisting cosmetic devices such that rather than owning multiple devices, a user can alternatively purchase an adapter assembly and drum assembly to use with a preexisting device. While FIG. 24 shows drum assembly 814 extending from a lateral side of device 810 by way of adapter assembly 850, according to various alternative embodiments, drum assembly 814 can be operationally coupled to device 810 using other suitable means. One embodiment of a device with which adapter assembly 850 and drum assembly 814 may be usable is shown in U.S. Pat. No. 8,551,117, which is incorporated by reference herein in its entirety.

Figure 27:
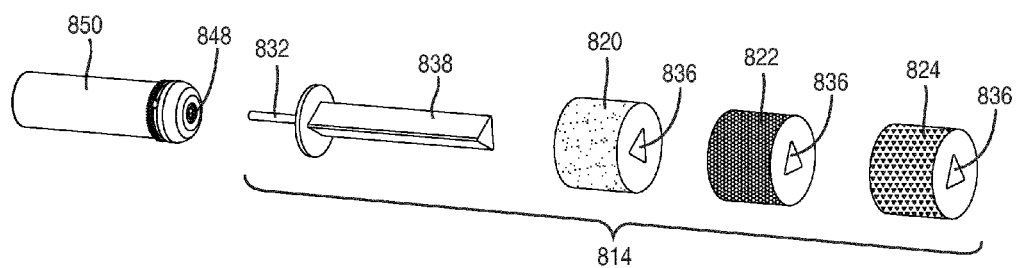
FIG. 27 is an exploded perspective view of the drum assembly of FIG. 24

Referring now to FIG. 27, according to one embodiment, drum assembly 814 includes a first drum portion 820, a second drum portion 822, and a third drum portion 824. First portion 820, second portion 822, and third portion 824 provide different characteristics for a user. In one embodiment, first portion 820, second portion 822, and third portion 824 have different hardnesses (e.g., differing characteristics regarding compressibility, deformation, flexibility, etc.). In other embodiments, the portions can differ in abrasiveness. In some embodiments, first portion 820, second portion 822, and third portion 824 can be provided with a visual indication such as a color, a stripe, etc. to provide an indication of the type of abrasive, degree of abrasiveness, relative hardness, deformability, flexibility etc. As can be seen in FIG. 27, first portion 820, second portion 822, and third portion 824 each include an aperture 836 configured to receive a shaft 838. In one embodiment, apertures 836 and shaft 838 are generally triangular. In other embodiments, shaft 838 and apertures 836 may be otherwise shaped (e.g., square, hexagonal, round, oval, etc.). While FIGS. 24-27 show drum assembly 814 as including three portions, according to various alternative embodiments, more or fewer portions can be utilized (e.g., 1, 2, 4, etc.).

Figure 28:
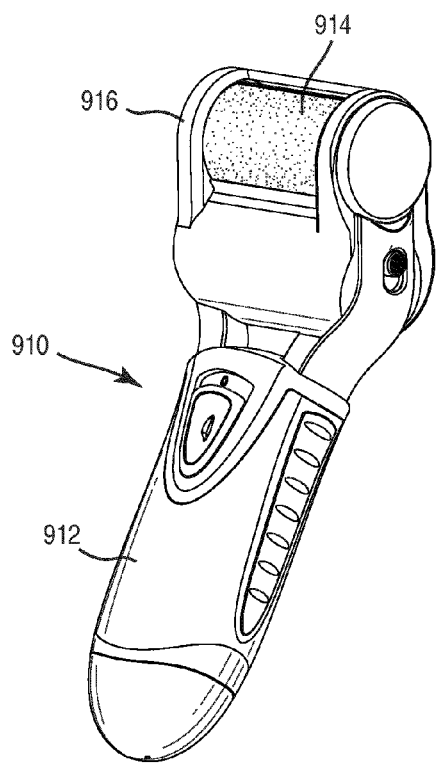
FIG. 28 is a perspective view of a drum assembly coupled to a cosmetic device, according to another embodiment.
Figure 29:
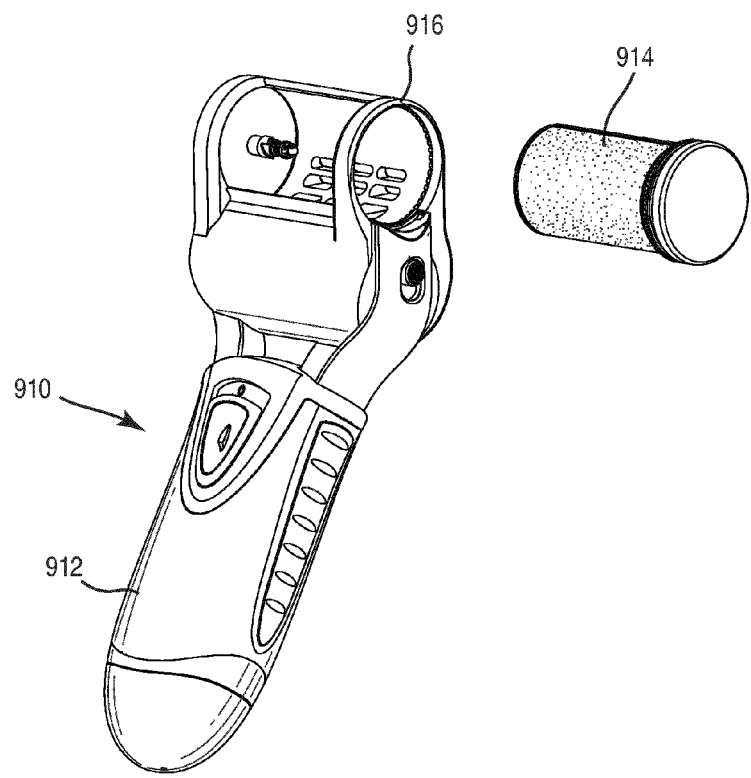
FIG. 29 is an exploded perspective view of the drum assembly and cosmetic device of FIG. 28.

As can be seen in FIGS. 28-29, a drum assembly 914 may be usable in another embodiment in a device 910. Device 910 includes a housing with a handle portion 912 and a head mounting bracket 916 supporting drum assembly 914. When drum assembly 914 is coupled to mounting bracket 16 at least a portion of drum assembly 914 is exposed. Drum assembly 914 includes a drum similar to drum 30 described above and includes an outer surface or layer and an inner, deformable layer or portion. The outer surface is configured to smooth and or polish skin, material from a fingernail, toenail, or other surface in order to exfoliate and/or smooth and/or shine the surface. In one embodiment, drum assembly 914 is configured to be inserted and/or removed in a lateral direction, permitting the drum or its outer surface to be cleaned, maintained, replaced, etc. In one embodiment, device 910 may include a plurality of drum assemblies 914, each having different abrasive outer surfaces providing different levels of coarseness or abrasiveness, or alternatively, differing levels of compressibility. In this embodiment, the user may select and install a drum assembly 914 depending on the user's desire or need for a particular use. Further, drum assembly 914 may be configured to allow the user to easily switch or replace drum assembly 914. In further embodiments, different portions of drum assembly 914 include differing levels of abrasiveness and/or compressibility, to provide different smoothing and/or polishing features on a single drum.

It should be understood that the construction and arrangement of the elements of the various embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. Some like components have been described in the present disclosure using the same reference numerals in different figures. This should not be construed as an implication that these components are identical in all embodiments; various modifications may be made in various different embodiments. It should be noted that the components and/or assemblies disclosed herein may be constructed from any of a wide variety of materials that provide sufficient strength or durability, in any of a wide variety of colors, textures, and combinations.

What is claimed is:

1. A handheld cosmetic device, comprising:
   an axially extending body defining an outer periphery in a circumferential direction and having:
   a first end;
   a second end axially opposite the first end and configured to receive a roller assembly; and
   a first portion between the first end and the second end, the first portion defining a first receptacle configured to receive a battery; and
   a shell removably coupled to the body, the shell having a closed end and at least one sidewall extending from the closed end and around the outer periphery of the body to at least partially define a cavity configured to receive the body and extending axially from the first end to substantially beyond the first portion such that the closed end is adjacent the first end of the body; and
   a shield extending upward from the body and configured to extend about less than one-half of the circumference of the roller assembly;
   a cover removably coupled to the body, wherein the cover includes a cutout to receive the shield such that the cover, the shield and the body collectively enclose the roller assembly when the cover is coupled to the body.

2. The cosmetic device of claim 1, further comprising the roller assembly, wherein the roller assembly includes one of a sheet of abrasive material and a coating of abrasive material.

3. The cosmetic device of claim 1, further comprising the roller assembly, wherein the roller assembly includes a generally cylindrical drum, the drum including an abrasive outer surface and a deformable portion disposed beneat the abrasive outer surface.

4. The cosmetic device of claim 3, wherein the deformable portion is configured such that the abrasive outer surface and the deformable portion deform upon application of pressure during use of the cosmetic device on a nail of a user.

5. The cosmetic device of claim 3, wherein the deformable portion includes a first cylindrical portion having a first compressibility and a second cylindrical portion having a second compressibility different from the first cylindrical portion.

6. The cosmetic device of claim 1, wherein the roller assembly includes a first portion having a first abrasiveness and a second portion having a second abrasiveness different from the first abrasiveness.

7. The cosmetic device of claim 6, wherein the first portion includes a first visual indication of the first abrasiveness and the second portion includes a second visual indication of the second abrasiveness.

8. A cosmetic device, comprising:
   a shell defining a lower periphery of the cosmetic device, the shell being elongated in a first direction and configured to be held in the hand of a user;

a flange portion positioned adjacent an upper portion of the shell, wherein an outer surface of the flange portion and an outer surface of shell form a first substantially smooth transition;

a drive mechanism provided within the shell;

an abrasive member operatively coupled to the drive mechanism and extending in the first direction away from a first side of the flange portion, wherein the abrasive member is usable to remove skin or nail material of a user when the drive mechanism drives the abrasive member;

a shield member positioned to the first side of the flange portion and extending in the first direction, wherein the shield member includes at least one curved portion;

a cover member configured to be movable along the first direction relative to the shell and the flange portion between an attached configuration and a detached configuration, wherein when the cover is in the attached configuration, the at least one curved portion of the shield member and the abrasive member are concealed from view, and the cover and the flange portion form a second substantially smooth transition; and a power switch disposed adjacent an edge of the flange portion and at least partially within a U-shaped recess in the shell, wherein the power switch is slidable to turn the drive mechanism on and off.

* * * * *